(12) United States Patent
Yang

(10) Patent No.: US 6,440,081 B1
(45) Date of Patent: Aug. 27, 2002

(54) INSTRUMENT FOR MEASURING BLOOD PRESSURE AND TEMPERATURE

(75) Inventor: Paul Yang, Chung-Ho (TW)

(73) Assignee: Health & Life Co., Ltd., Taipei Hsien (TW)

( * ) Notice: Subject to any disclaimer, the term of this patent is extended or adjusted under 35 U.S.C. 154(b) by 0 days.

(21) Appl. No.: 09/796,895

(22) Filed: Mar. 2, 2001

(51) Int. Cl.[7] .................................................. A61B 5/00
(52) U.S. Cl. ........................ 600/503; 600/500; 600/549
(58) Field of Search ............................ 600/301, 549, 600/485, 500–503

(56) References Cited

U.S. PATENT DOCUMENTS

| | | | | |
|---|---|---|---|---|
| 4,116,228 A | * | 9/1978 | Hudspeth | 600/301 |
| 4,121,574 A | * | 10/1978 | Lester | 600/549 |
| 4,270,547 A | * | 6/1981 | Steffan et al. | 600/301 |
| 4,974,607 A | * | 12/1990 | Miwa | 600/485 |
| 6,146,015 A | * | 11/2000 | Weiss | 600/549 |

* cited by examiner

*Primary Examiner*—Robert L. Nasser
(74) *Attorney, Agent, or Firm*—Finnegan, Henderson, Farabow, Garrett & Dunner, L.L.P.

(57) ABSTRACT

An instrument for measuring blood pressure and temperature includes a digital sphygmomanometer, a digital thermometer, and a transmission device. The digital sphygmomanometer includes a housing formed with a thermometer-receiving groove, and a control unit mounted in the housing. The control unit is operable so as to activate an air pump unit and obtain pressure information corresponding to air pressure inside a pneumatic wristlet and so as to activate a display unit to show the blood pressure information thereon. The digital thermometer is fitted removably in the thermometer-receiving groove, and includes a processor that is operable so as to obtain temperature information from a temperature probe and so as to activate a display panel to show the temperature thereon. The transmission device is provided on the digital sphygmomanometer and the digital thermometer for establishing a communications link between the control unit and the processor. The control unit is operable so as to receive the temperature information from the processor via the transmission device and to enable the display unit to show the temperature information thereon.

4 Claims, 5 Drawing Sheets

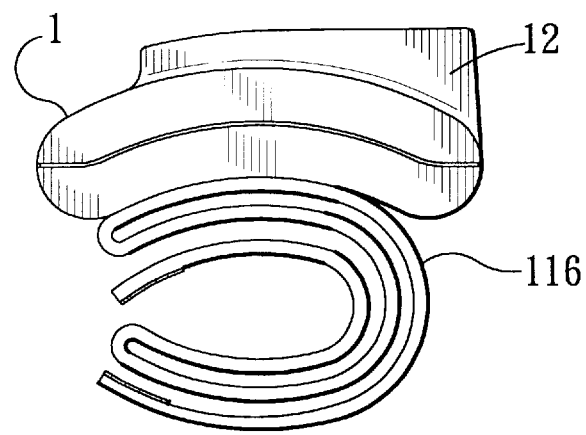
F I G. 1
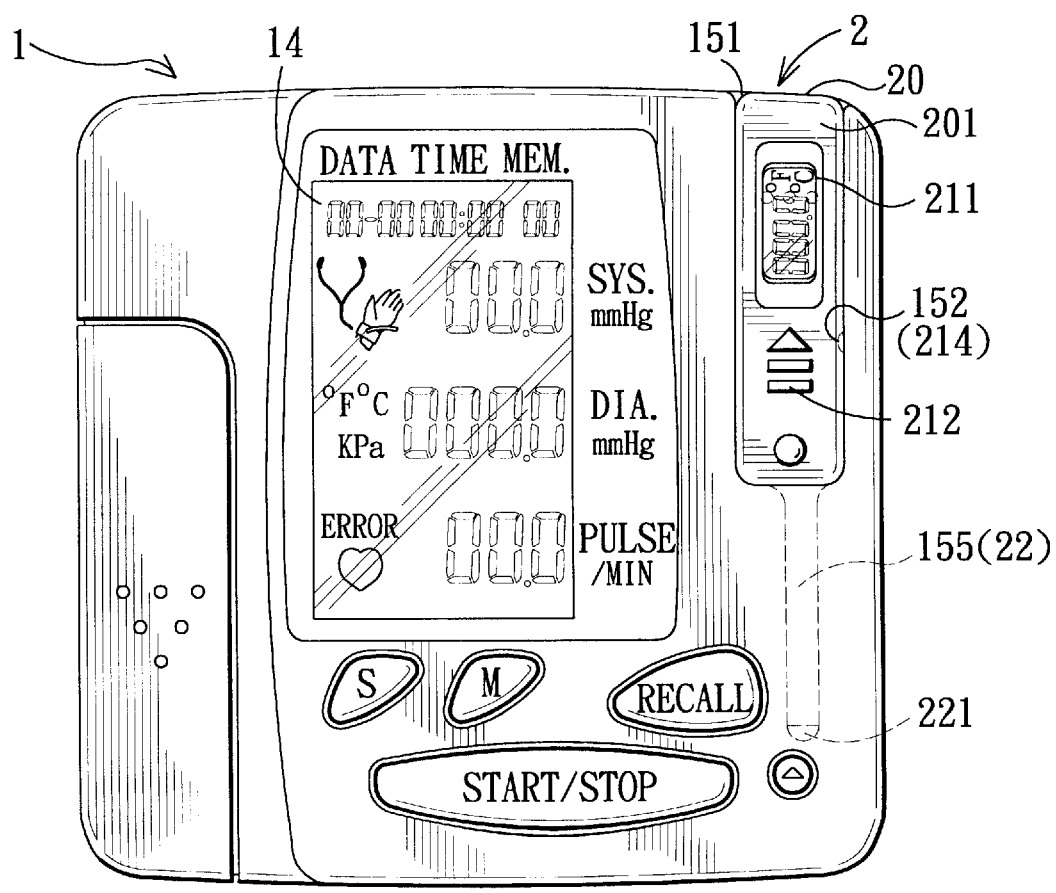
F I G. 2

INSTRUMENT FOR MEASURING BLOOD PRESSURE AND TEMPERATURE

BACKGROUND OF THE INVENTION

1. Field of the Invention

The invention relates to an instrument for measuring blood pressure and temperature, more particularly to an instrument for measuring blood pressure and temperature that can show temperature information from a digital thermometer on a digital sphygmomanometer.

2. Description of the Related Art

In co-pending U.S. patent application Ser. No. 09/392492, the applicant. disclosed a touch-control digital sphygmomanometer which includes a pneumatic wristlet, a housing, an air pump unit, a pressure sensing unit, a control unit, a display panel, and a touch-control panel. The disclosure of the aforesaid co-pending U.S. patent application is incorporated herein by reference.

A conventional digital thermometer includes processor mounted in a casing, a display unit mounted on the casing, and a sensing unit provided with a temperature probe. The processor is operable so as to enable the display unit to show temperature information from the temperature probe thereon. Since the casing is elongated, the size of the display unit is limited to that of the casing, thereby resulting in inconvenience when reading the temperature information. Furthermore, due to the small size of the conventional digital thermometer, misplacement of the same can easily occur.

SUMMARY OF THE INVENTION

Therefore, the object of the present invention is to provide an instrument for measuring blood pressure and temperature that can show temperature information from a digital thermometer on a digital sphygmomanometer.

According to the present invention, an instrument for measuring blood pressure and temperature comprises:

a digital sphygmomanometer including a pneumatic wristlet, a housing formed with a thermometer-receiving groove, an air pump unit mounted on the housing and in fluid communication with the pneumatic wristlet, the air pump unit being adapted to pump air into the pneumatic wristlet when activated, a control unit mounted in the housing and coupled electrically to the air pump unit, the control unit being operable so as to activate the air pump unit and obtain blood pressure information corresponding to air pressure inside the pneumatic wristlet, and a display unit mounted on the housing and coupled electrically to the control unit, the control unit being operable so as to activate the display unit to show the blood pressure information thereon;

a digital thermometer fitted removably in the thermometer-receiving groove and including a sensing portion provided with a temperature probe, a processor coupled electrically to the temperature probe to receive a temperature signal therefrom, the processor being operable so as to obtain temperature information from the temperature signal, and a display panel coupled electrically to the processor, the processor being operable so as to activate the display panel to show the temperature information thereon; and a transmission device provided on the digital sphygmomanometer and the digital thermometer for establishing a communications link between the control unit and the processor, the control unit being operable so as to receive the temperature information from the processor via the transmission device and to enable the display unit to show the temperature information thereon.

BRIEF DESCRIPTION OF THE DRAWINGS

Other features and advantages of the present invention will become apparent in the following detailed description of the preferred embodiments with reference to the accompanying drawings, of which:

FIG. 1 is a schematic. side view of the first preferred embodiment of an instrument for measuring blood pressure and temperature according to this invention;

FIG. 2 is a schematic top view of the first preferred embodiment;

DETAILED DESCRIPTION OF THE PREFERRED EMBODIMENTS

Figure 3:
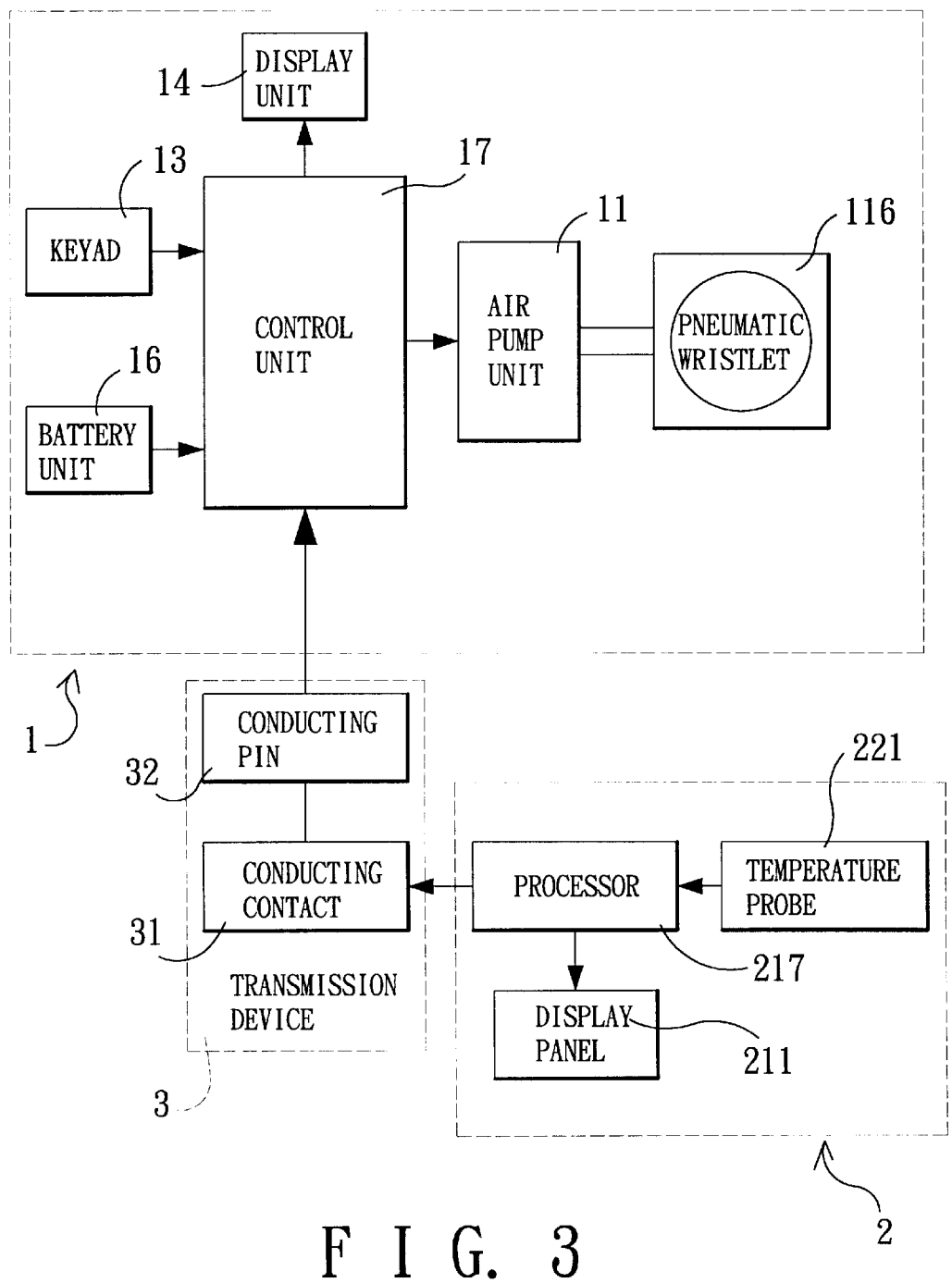
FIG. 3 is a schematic circuit block diagram illustrating the first preferred embodiment.

Before the present invention is described in greater detail, it should be noted that like elements are denoted by the same reference numerals throughout the disclosure.

Referring to FIGS. 1 to 3, according to the first preferred embodiment of this invention, an instrument for measuring blood pressure and temperature is shown to include a digital sphygmomanometer 1, a digital thermometer 2, and a transmission device 3.

Figure 4:
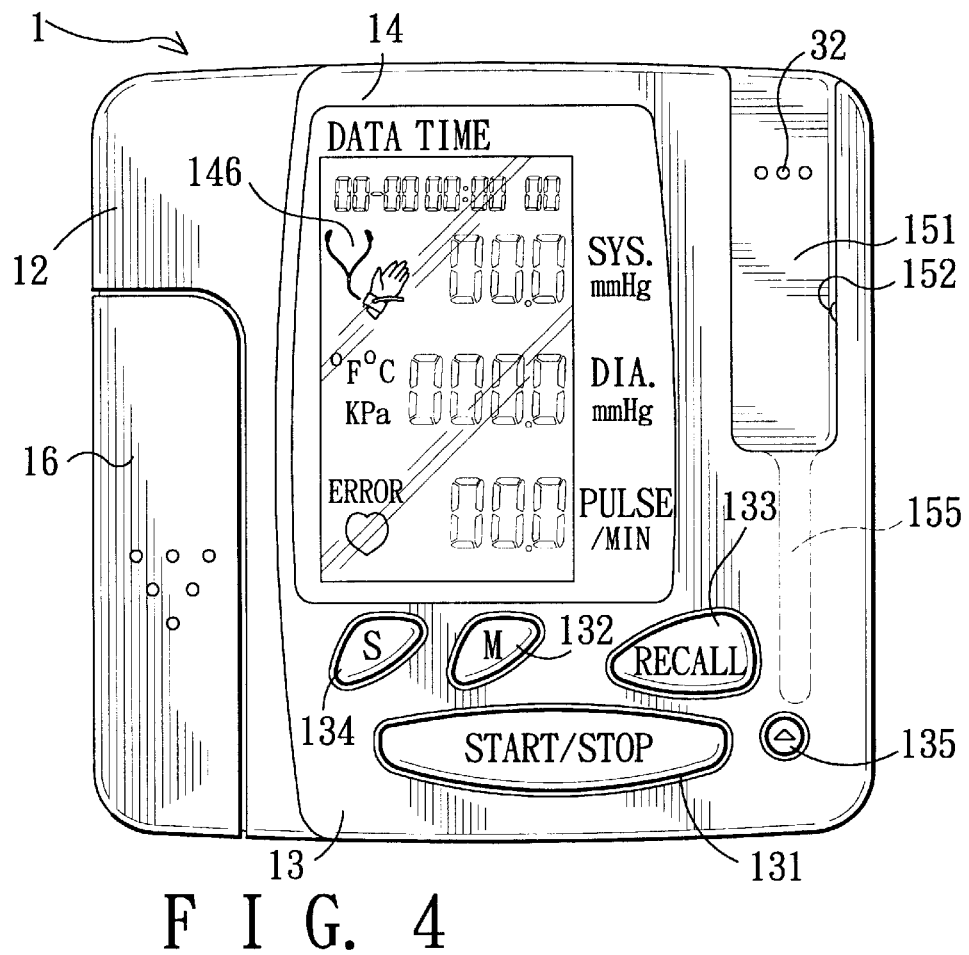
FIG. 4 is a schematic top view of a digital sphygmomanometer of the first preferred embodiment.

With reference to FIGS. 3 and 4, the digital sphygmomanometer 1 includes a pneumatic wristlet 116, a housing 12 formed with a thermometer-receiving groove 151, an air pump unit 11 mounted on the housing 12 and in fluid communication with the pneumatic wristlet 116, a control unit 17 mounted in the housing 12 and coupled electrically to the air pump unit 11, a display unit 14 mounted on the housing 12 and coupled electrically to the control unit 17, a keypad 13 mounted on the housing 12 and coupled electrically to the control unit 17, and a battery unit 16 mounted in the housing 12 and coupled electrically to the control unit 17. The air pump unit 11 is adapted to pump air into the pneumatic wristlet 116 when activated. The control unit 17 is operable so as to activate the air pump unit 11 and obtain blood pressure information corresponding to air pressure inside the pneumatic wristlet 116. The control unit 17 is operable so as to activate the display unit 14 to show the blood information, such as the values of systolic pressure, diastolic pressure and heartbeat, thereon. The keypad 13 includes a plurality of function keys, such as a START/STOP key 131, a MODE (M) key 132, a RECALL key 133, a SET (S) key 134, and an adjust key 135.

In this embodiment, the digital sphygmomanometer 1 further provides a warning function. Prior to using the digital sphygmomanometer 1, predetermined reference values of systolic pressure, diastolic pressure and heartbeat can be preset by pressing the "S" key 134 and the adjust key 135. During use, when any one of the measured values of systolic pressure, diastolic pressure and heartbeat is greater than a corresponding one of the predetermined reference values of systolic pressure, diastolic pressure and heartbeat, a flashing symbol 146 that serves as a warning signal is shown on the display unit 14.

With reference to FIGS. 2 and 3, the digital thermometer 2 includes a casing 20 fitted removably in the thermometer-receiving groove 151, a sensing portion 22 extending outwardly of the casing 20 and provided with a temperature probe 221, a processor 217, and a display panel 211. The casing 20 has top and bottom surfaces 201, 202. The thermometer-receiving groove 151 has an end portion formed with a blind hole 155 for receiving the sensing portion 22. The processor 217 is mounted in the casing 20, and is coupled electrically to the temperature probe 221 to receive a temperature signal therefrom. The processor 217 is operable so as to obtain temperature information from the temperature signal. The display panel 211 is mounted on the top surface 201 of the casing 20 and is coupled electrically to the processor 217. The processor 217 is operable so as to activate the display panel 211 to show the temperature information thereon.

Figure 5:
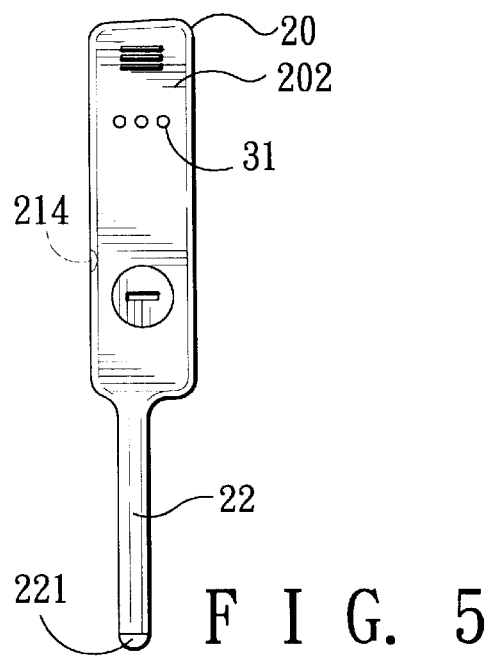
FIG. 5 is a schematic bottom view of a digital thermometer of the first preferred embodiment.

A plurality of projecting ribs 212 are provided on the top surface 201 of the casing 20 to facilitate removal of the digital thermometer 2 from the thermometer-receiving groove 151. A retaining device includes a projection 152 provided in the thermometer-receiving groove 151, as best shown in FIG. 4, and a recess 214 formed in the casing 20, as best shown in FIG. 5. When the digital thermometer 2 is fitted in the thermometer-receiving groove 151, the projection 152 and the recess 214 engage each other for retaining releasably the digital thermometer 2 in the thermometer-receiving groove 151.

The transmission device 3 is provided on the digital sphygmomanometer 1 and the digital thermometer 2 for establishing a communications link between the control unit 17 and the processor 217. The control unit 17 is operable so as to receive the temperature information from the processor 217 via the transmission device 3 and to enable the display unit 14 to show the temperature information thereon. The temperature information from the processor 217 and the blood pressure information are shown on a display region of the display unit 14. In this embodiment, the transmission device 3 includes a plurality of conducting contacts 31 provided on the bottom surface 202 of the casing 20 of the digital thermometer 2, as shown in FIG. 5, and coupled electrically to the processor 217, and a plurality of conducting pins 32 provided in the thermometer-receiving groove 151 of the housing 15, as shown in FIG. 4, and coupled electrically to the control unit 17. The conducting contacts 31 are in contact with the conducting pins 32, respectively, when the digital thermometer 2 is fitted in the thermometer-receiving groove 151.

Figure 6:
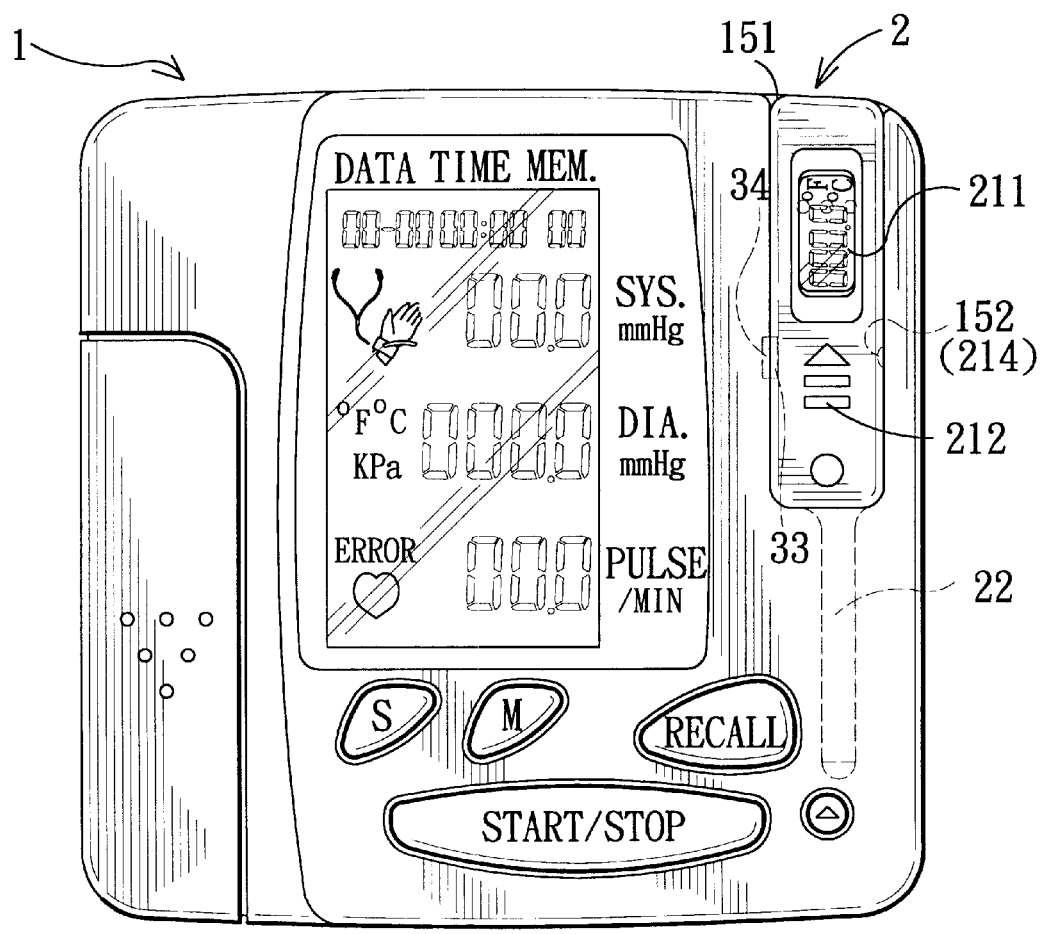
FIG. 6 is a schematic top view of the second preferred embodiment of an instrument for measuring blood pressure and temperature according to this invention.
Figure 7:
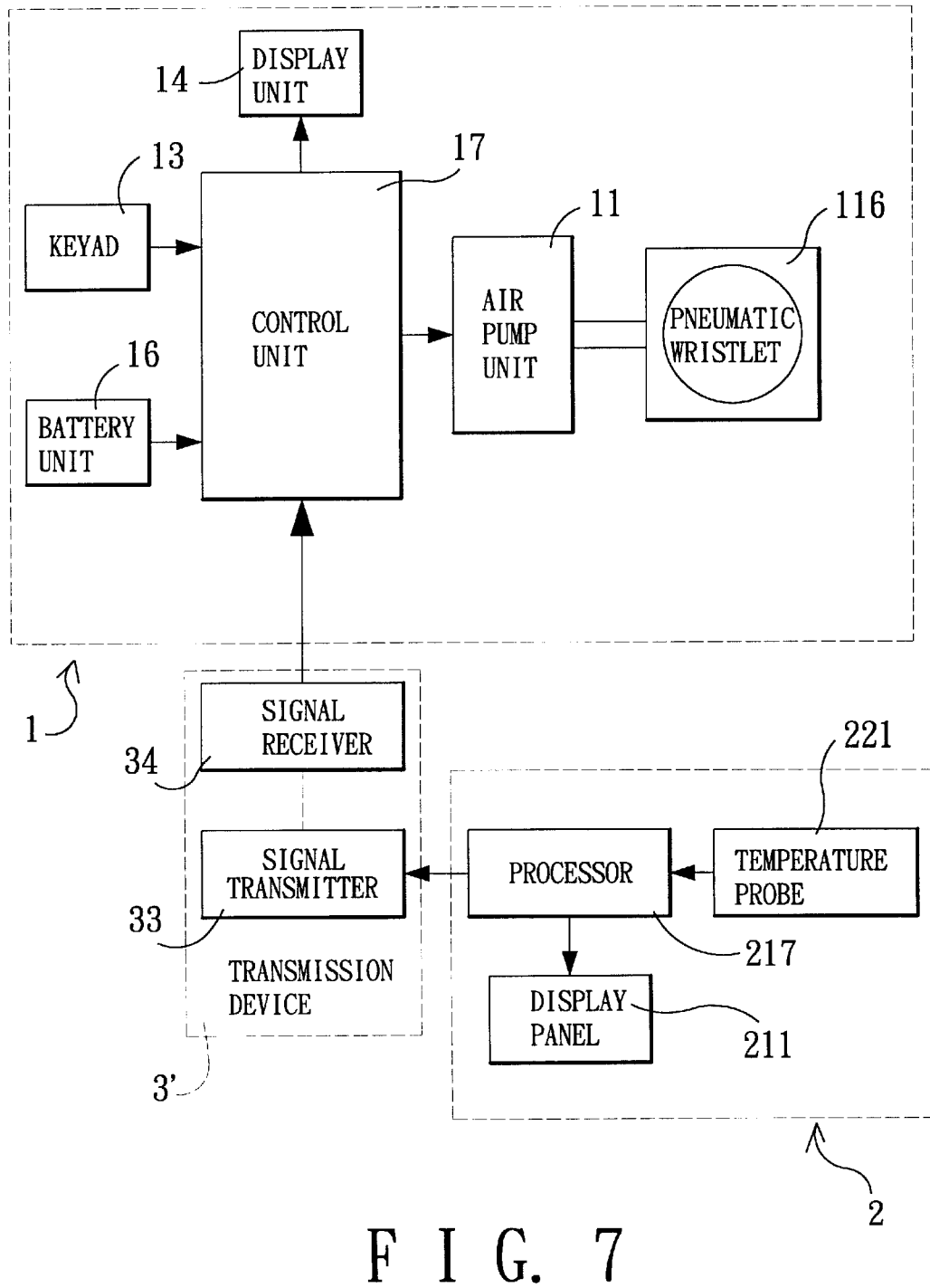
FIG. 7 is a schematic circuit block diagram illustrating the second preferred embodiment.

FIGS. 6 and 7 illustrate the second preferred embodiment of the present invention, which is a modification of the first preferred embodiment. Unlike the previous embodiment, the transmission device 3' includes a signal transmitter 33 provided on the casing 20 of the digital thermometer 2 and coupled electrically to the processor 217, and a signal receiver 34 provided on the housing 12 and coupled electrically to the control unit 17. The signal transmitter 33 is operable so as to transmit wirelessly the temperature information for reception by the control unit 17 via the signal receiver 34.

Due to the presence of the transmission device 3, 3', the temperature information from the processor 217 can be received by the control unit 17 such that the display unit 14 can be enabled by the control unit 17 to show the temperature information thereon. The control unit 17 is operable so as to record and recall the temperature information via the operation of keypad 13 for observation and reference. Furthermore, due to the engagement between the projection 152 and the recess 214 of the retaining device, the instrument of this invention can ensure proper positioning of the digital thermometer 2 in the thermometer-receiving groove 151. The object of the invention is thus met.

While the present invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

I claim:

1. An instrument for measuring blood pressure and temperature, comprising:
    a digital sphygmomanometer including
        a pneumatic wristlet,
        a housing formed with a thermometer-receiving groove,
        an air pump unit mounted on said housing and in fluid communication with said pneumatic wristlet, said air pump unit being adapted to pump air into said pneumatic wristlet when activated,
        a control unit mounted in said housing and coupled electrically to said air pump unit, said control unit being operable so as to activate said air pump unit and obtain blood pressure information corresponding to air pressure inside said pneumatic wristlet, and
        a display unit mounted on said housing and coupled electrically to said control unit, said control unit being operable so as to activate said display unit to show the blood pressure information thereon;
    a digital thermometer fitted removably in said thermometer-receiving groove and including
        a sensing portion provided with a temperature probe,
        a processor coupled electrically to said temperature probe to receive a temperature signal therefrom, said processor being operable so as to obtain temperature information from the temperature signal, and
        a display panel coupled electrically to said processor, said processor being operable so as to activate said display panel to show the temperature information thereon; and
    a transmission device provided on said digital sphygmomanometer and said digital thermometer for establishing a communications link between said control unit and said processor, said control unit being operable so as to receive the temperature information from said processor via said transmission device and to enable said display unit to show the temperature information thereon.

2. The instrument of claim 1, wherein said transmission device includes a conducting contact provided on said digital thermometer and coupled electrically to said processor, and a conducting pin provided in said thermometer-receiving groove of said housing and coupled electrically to said control unit, said conducting contact being in contact with said conducting pin when said digital thermometer is fitted in said thermometer-receiving groove.

3. The instrument of claim 1, wherein said transmission device includes a signal transmitter provided on said digital thermometer and coupled electrically to said processor, and a signal receiver provided on said housing and coupled electrically to said control unit, said signal transmitter being operable so as to transmit wirelessly the temperature information for reception by said control unit via said signal receiver.

4. The instrument of claim 1, further comprising a retaining device for retaining releasably the digital thermometer in said thermometer-receiving groove.

* * * * *